United States Patent
Tirumala et al.

(10) Patent No.: US 8,738,302 B2
(45) Date of Patent: May 27, 2014

(54) ANALYZING AN ACOUSTIC WAVE THAT HAS PROPAGATED THROUGH A BODY OF WATER WHILE THE BODY OF WATER IS BEING FROZEN

(75) Inventors: Ramesh B. Tirumala, Libertyville, IL (US); Raymond R. Haack, Mishicot, WI (US); William E. Smith, Jr., Sheboygan, WI (US); Lee G. Mueller, Kewaunee, WI (US)

(73) Assignee: Manitowoc Foodservice Companies, LLC, Manitowoc, WI (US)

( * ) Notice: Subject to any disclaimer, the term of this patent is extended or adjusted under 35 U.S.C. 154(b) by 365 days.

(21) Appl. No.: 13/196,557

(22) Filed: Aug. 2, 2011

(65) Prior Publication Data

US 2012/0197543 A1  Aug. 2, 2012

Related U.S. Application Data (60) Provisional application No. 61/370,047, filed on Aug. 2, 2010, provisional application No. 61/379,220, filed on Sep. 1, 2010.

(51) Int. Cl.
*G06F 19/00* (2011.01)
*F25C 1/12* (2006.01)

(52) U.S. Cl.
CPC .................................. *F25C 1/12* (2013.01)
USPC ........................................................ 702/25

(58) Field of Classification Search
CPC ........................................................ F25C 1/12
USPC ........................................................ 702/25
See application file for complete search history.

(56) References Cited

U.S. PATENT DOCUMENTS

| 4,628,736 | A | 12/1986 | Kirby et al. |
| 4,697,254 | A | 9/1987 | Pridham |
| 5,627,310 | A | 5/1997 | Johnson |
| 6,328,467 | B1 | 12/2001 | Keyhani |
| 6,612,156 | B1 | 9/2003 | Hakimuddin |
| 6,678,209 | B1 * | 1/2004 | Peng et al. ............ 367/95 |

(Continued)

FOREIGN PATENT DOCUMENTS

| CN | 101680693 A | 3/2010 |
| JP | 19902212734 A | 2/1990 |
| WO | 2008/144864 A1 | 12/2008 |

OTHER PUBLICATIONS

International Preliminary Report on Patentability dated Dec. 7, 2012 from corresponding International Patent Application No. PCT/US11/046298, 4 pages.
International Search Report and Written Opinion dated Nov. 30, 2011 for corresponding International Patent Application No. PCT/US2011/046298.

(Continued)

*Primary Examiner* — Bryan Bui
(74) *Attorney, Agent, or Firm* — Ohlandt, Greeley, Ruggiero & Perle, LLP (57) ABSTRACT

A method that includes: (i) detecting an acoustic wave that is propagating through a body of water, as the body of water is being frozen on a structure, thus yielding a detected acoustic wave; (ii) extracting, from the detected acoustic wave, (a) a frequency component thereof, and (b) a magnitude of the frequency component; and (iii) removing the body of water from the structure when the magnitude exceeds a threshold value.

10 Claims, 9 Drawing Sheets

(56) References Cited

U.S. PATENT DOCUMENTS

| | | |
|---|---|---|
| 7,190,011 B2 | 3/2007 | Aizawa et al. |
| 7,350,367 B2 | 4/2008 | Matsiev et al. |
| 7,765,814 B2 | 8/2010 | Goldstein |
| 2006/0150738 A1 | 7/2006 | Leigh |
| 2006/0218945 A1 | 10/2006 | Goldstein |
| 2008/0029245 A1 | 2/2008 | Goldstein |

OTHER PUBLICATIONS

Chinese Office Action dated Aug. 14, 2013 for Chinese application No. 201110060600.3.
Chinese Office Action dated Aug. 23, 2013 for Chinese application No. 201110060547.7.
Japanese Office Action dated Feb. 25, 2014 for Japanese application No. 2013-523282.

* cited by examiner

ANALYZING AN ACOUSTIC WAVE THAT HAS PROPAGATED THROUGH A BODY OF WATER WHILE THE BODY OF WATER IS BEING FROZEN

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field

The present disclosure relates to an ice-making machine, and more particularly, to an analysis of an acoustic wave that is propagating through a body of water in the ice-making machine. The analysis recognizes when the body of water is frozen, so that the body of water can be harvested, as ice, from the ice-making machine. The analysis also diagnoses operations of devices in the ice-making machine.

2. Description of the Related Art

The approaches described in this section are approaches that could be pursued, but not necessarily approaches that have been previously conceived or pursued. Therefore, unless otherwise indicated, the approaches described in this section may not be prior art to the claims in this application and are not admitted to be prior art by inclusion in this section.

For efficient operation of an ice-making machine, it is desirable to remove the ice, also known as harvesting the ice, soon after the ice has fully formed. Such harvesting of the ice allows for a new body of water to be introduced so that a new body of ice can be formed, thus maximizing the usage of the ice-making machine.

One technique for recognizing the readiness of the ice for harvesting is to monitor a magnitude of a mechanical vibration that is propagating through a body of water as the body of water is being frozen. At a point in time when the magnitude exceeds a predetermined threshold, the body of water is assumed to be adequately frozen, and so, is harvested.

This existing technique uses only amplitude change above a set threshold to detect ice formation. This technique has a drawback in that it does not distinguish between various possible sources of mechanical vibrations, and so, cannot determine whether the change is due to a change in acoustics of the ice-making machine or spurious acoustics in an ambient noise environment. Consequently, the existing technique does not necessarily initiate harvesting at a most optimum time, and therefore, the ice-making machine may be operating at a less than optimum level of efficiency.

SUMMARY

There is provided a method that includes: (i) detecting an acoustic wave that is propagating through a body of water, as the body of water is being frozen on a structure, thus yielding a detected acoustic wave; (ii) extracting, from the detected acoustic wave, (a) a frequency component thereof, and (b) a magnitude of the frequency component; and (iii) removing the body of water from the structure when the magnitude exceeds a threshold value.

There is also provided a method that includes: (a) detecting an acoustic wave that is propagating through a body of water, as the body of water is being frozen on a structure in an ice-making machine, thus yielding a detected acoustic wave; (b) analyzing the detected acoustic wave to yield a spectrum thereof; (c) determining whether the spectrum includes a spectral signature, thus yielding a determination, wherein the spectral signature is present when a device in the ice-making machine is operating; and (d) issuing an alert based on the determination.

BRIEF DESCRIPTION OF THE DRAWINGS

A component or a feature that is common to more than one drawing is indicated with the same reference number in each of the drawings.

DESCRIPTION OF THE PREFERRED EMBODIMENT

Figure 1:
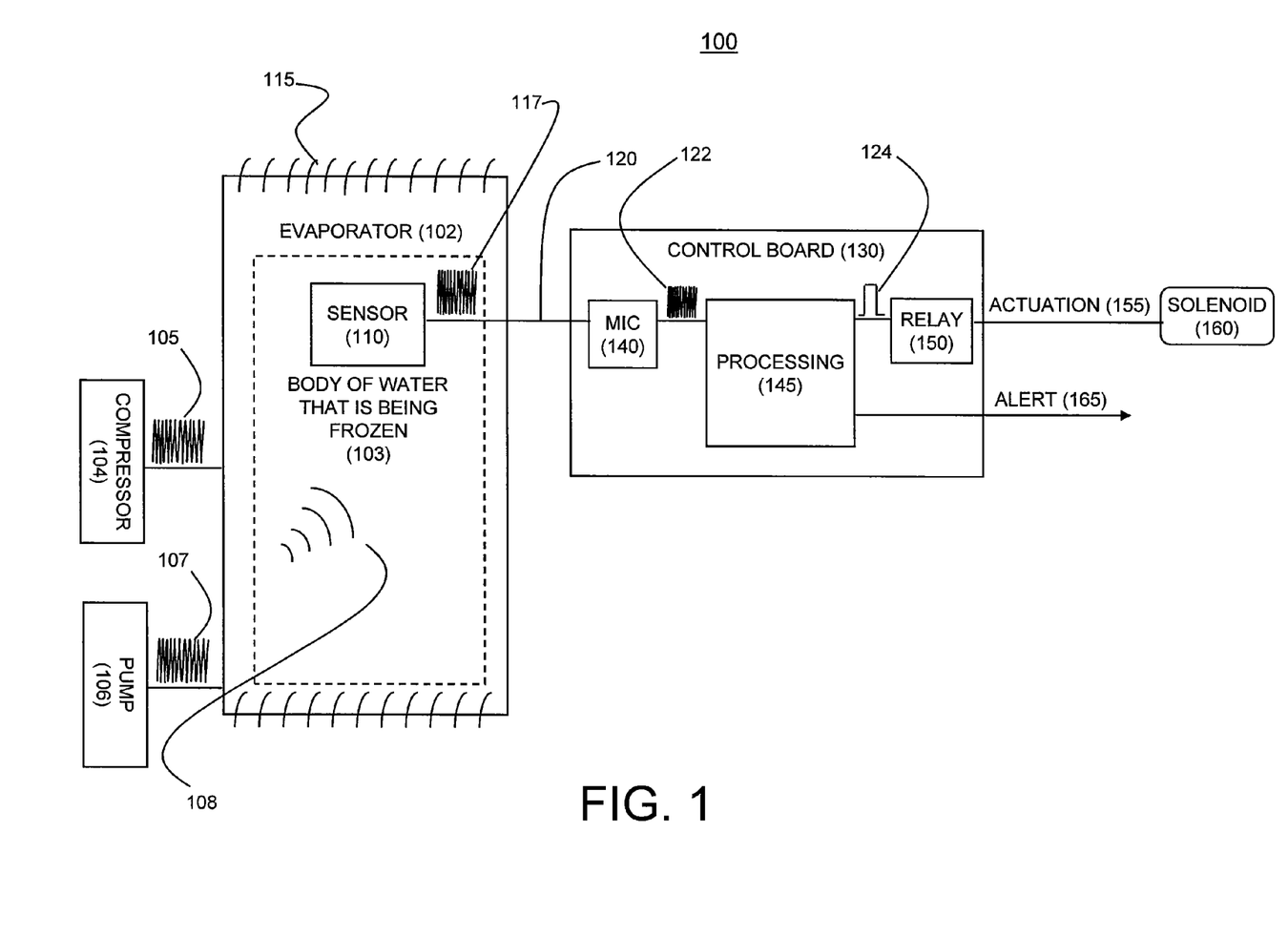
FIG. 1 is a functional block diagram of a system implemented in an ice-making machine.

FIG. 1 is a functional block diagram of a system, referred to herein as system 100, implemented in an ice-making machine. System 100 performs various digital signal processing operations on an acoustic signal from an ice thickness sensor, using a fast Fourier transform (FFT) algorithm, for increasing reliability of ice detection and for providing enhanced system diagnostics on the ice-making machine.

System 100 includes an evaporator 102, a compressor 104, a water pump, i.e., pump 106, a control board 130 and a solenoid 160. Evaporator 102 includes a sensor 110. Control board 130 includes a microphone 140, a processing module 145 and a relay 150. The term "module" is used herein to denote a functional operation that may be embodied either as a stand-alone component or as an integrated configuration of a plurality of sub-ordinate components.

System 100 runs through an ice-making cycle that includes a pre-chill stage, a freeze stage, a harvest stage and a purge stage.

Evaporator 102 is a structure for forming ice thereon. Pump 106 pumps and circulates water 115, in a liquid state, so that water 115 flows over evaporator 102 and collects as a body of water, i.e., water 103 (in FIG. 1, represented with a perimeter having a dashed line), that is being frozen into a solid state, i.e., ice.

Evaporator 102 has a coil (not shown) through which is routed either of a cold gas or a hot gas. Compressor 104 facilitates the routing of the cold gas through the coil. When the cold gas is routed through the coil, water 103 freezes, thus forming as ice on evaporator 102. In practice, water 115 cascades over evaporator 102, and freezes gradually, so that water 103 forms into a block of ice. After water 103 forms as ice, the hot gas is routed through the coil, thus heating evaporator 102 and slightly melting the ice so that the ice, and more particularly water 103 in the form of ice, can be removed.

Evaporator 102 may also include a grid (not shown) for holding water 103 and forming water 103 in the shape of cubes, or any other desired shape.

Compressor 104, during operation, emits a mechanical vibration 105, and pump 106, during operation, emits a mechanical vibration 107. Each of mechanical vibration 105 and mechanical vibration 107 propagates through physical structures in system 100, and through water 103, as an acoustic wave 108. Thus, acoustic wave 108 may include contributions from either or both of mechanical vibration 105 and mechanical vibration 107.

Sensor 110, e.g., a diaphragm having a dimple, is a detector that detects acoustic wave 108, thus yielding a detected acoustic wave 117. Sensor 110 may be situated, for example, on a surface of evaporator 102, or at any location at which it can receive and detect acoustic wave 108. An acoustic wave conduit 120, e.g., a plastic tube, couples detected acoustic wave 117 from sensor 110 to microphone 140. Microphone 140 converts detected acoustic wave 117 into an analog electrical signal 122. Processing module 145 receives analog electrical signal 122, converts it into a digital signal and analyzes it, thus effectively analyzing detected acoustic wave 117.

Processing module 145, based on its analysis of detected acoustic wave 117, determines whether water 103 has formed into ice, and if yes, issues a signal 124 to remove water 103, as ice, from evaporator 102. More particularly, when processing module 145 has determined that water 103 has formed into ice, processing module 145 issues signal 124 to relay 150, which in turn issues an actuation signal 155 that energizes solenoid 160. Energizing solenoid 160 causes the routing of the hot gas through the coil of evaporator 102, which causes water 103 to slightly melt and become free from evaporator 102. The removal of the ice is also referred to as harvesting.

As noted above, acoustic wave 108 may include contributions from either or both of mechanical vibration 105 and mechanical vibration 107. Accordingly, either of mechanical vibration 105 or mechanical vibration 107 could be the source of acoustic wave 108, and as such, could be the source of detected acoustic wave 117 for the analysis performed by processing module 145.

Each of mechanical vibration 105 and mechanical vibration 107 is unique, and as such, provides a unique spectral signature for each of compressor 104 and pump 106. Processing module 145 analyzes detected acoustic wave 117 and draws some conclusions about the operations of compressor 104 and pump 106. For example, processing module 145, by way of communications with other components of system 100, knows in which ice-making stage system 100 is operating, and also knows when compressor 104 should turn ON, and when compressor 104 should turn OFF. Accordingly, processing module 145, based on its analysis of detected acoustic wave 117, also determines whether compressor 104 turns ON or OFF at its appropriate times. If processing module 145 determines that compressor 104 is not operating properly, then processing module 145 issues an alert signal 165. Alert signal 165 could be manifested, for example, as a fault indicator on a user interface (not shown in FIG. 1). Processing module 145 makes a similar determination for the operation of pump 106, and alert signal 165 indicates the operating status of pump 106.

Figure 2:
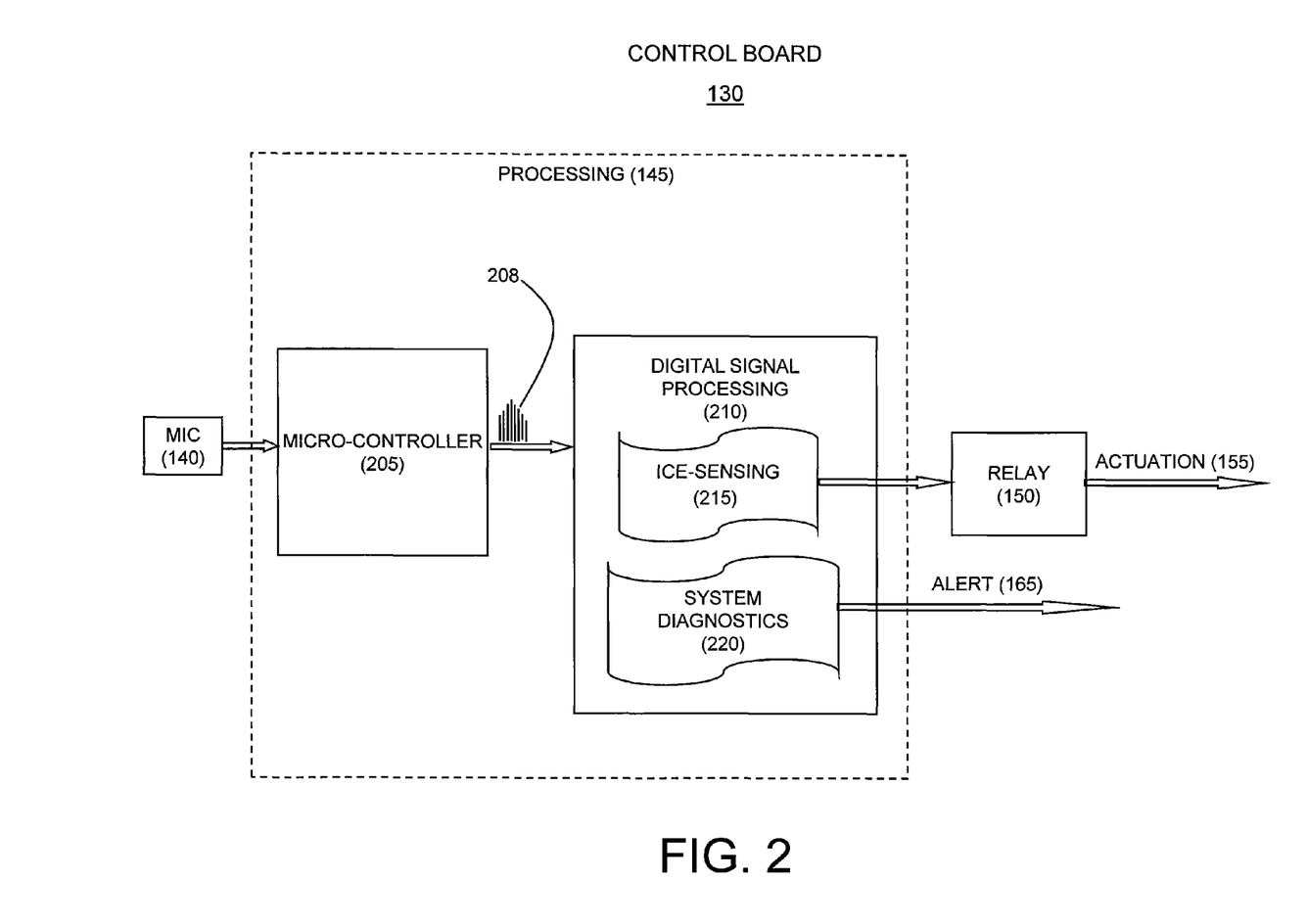
FIG. 2 is a functional block diagram of control board in the system of FIG. 1.

FIG. 2 is a functional block diagram of control board 130, and shows further details of processing module 145. Processing module 145 includes a micro-controller 205, and a digital signal processing module 210.

As noted above, processing module 145 receives analog electrical signal 122 from microphone 140. Micro-controller 205 includes analog circuitry (not shown) for amplifying and filtering analog electrical signal 122, and an analog-to-digital converter (A/D) (not shown) that converts analog electrical signal 122 to a digital signal 208. Thus, digital signal 208 is a digital representation of detected acoustic wave 117. Digital signal processing module 210 receives digital signal 208 and processes it in accordance with methods designated herein as an ice-sensing process 215 and a system diagnostics process 220.

In accordance with ice-sensing process 215, digital signal processing module 210 analyzes digital signal 208 to determine whether water 103 has formed into ice, and if yes, issues signal 124 to relay 150, which in turn issues actuation signal 155. Ice-sensing process 215 is described in greater detail below, with reference to FIGS. 3A and 3B.

In accordance with system diagnostics process 220, digital signal processing module 210 analyzes digital signal 208 to draw conclusions about the operations of compressor 104 and pump 106, and if necessary, issues alert signal 165. System diagnostics process 220 is described in greater detail below, with reference to FIG. 4.

In some situations, issues can occur in transmitting sound through tubes or connectors, or through a component making inadvertent contact with another component. Such an issue can trigger a false harvest signal. These issues can be avoided by embedding microphone 140 in a probe with sensor 110, i.e., an integrated sensor microphone, that comes into contact with the ice (i.e., the body of water) or the evaporator, or is situated in close proximity, e.g., less than 0.5 inches, to the ice (i.e., the body of water) or the evaporator.

For example, in the context of the components shown in FIG. 1, microphone 140 and sensor 110 could be integrated together, thus resulting in an integrated sensor microphone. Accordingly, there will be no need for microphone 140 on control board 130, and no need for acoustic wave conduit 120. The integrated sensor microphone avoids issues with transmission of sound from sensor 110 to microphone 140, and thus eliminates any chance of extraneous noise and vibration through acoustic wave conduit 120 to control board 130, and improves the signal to noise ratio. Additionally, the entire integrated sensor microphone can be hermetically sealed to eliminate any chance of moisture entering sensor 110 or microphone 140, and thus adversely impacting the performance of sensor 110 or microphone 140.

An alternative to the integrated sensor microphone is an integrated sensor accelerometer that employs an accelerometer instead of microphone 140. In the integrated sensor accelerometer, the accelerometer is used to measure the vibration transmitted through sensor 110. The accelerometer converts the vibration energy into an electrical signal that is transmitted to control board 130.

Either of the integrated sensor microphone or the integrated sensor accelerometer could be regarded as a sensing probe, and be situated on evaporator 102 in place of the stand-alone sensor 110. The sensing probe produces an electrical signal, similar to analog electrical signal 122, that is coupled into processing module 145. An exemplary embodiment of such a sensing probe is described in greater detail below, with reference to FIGS. 6-8.

Figure 3A:
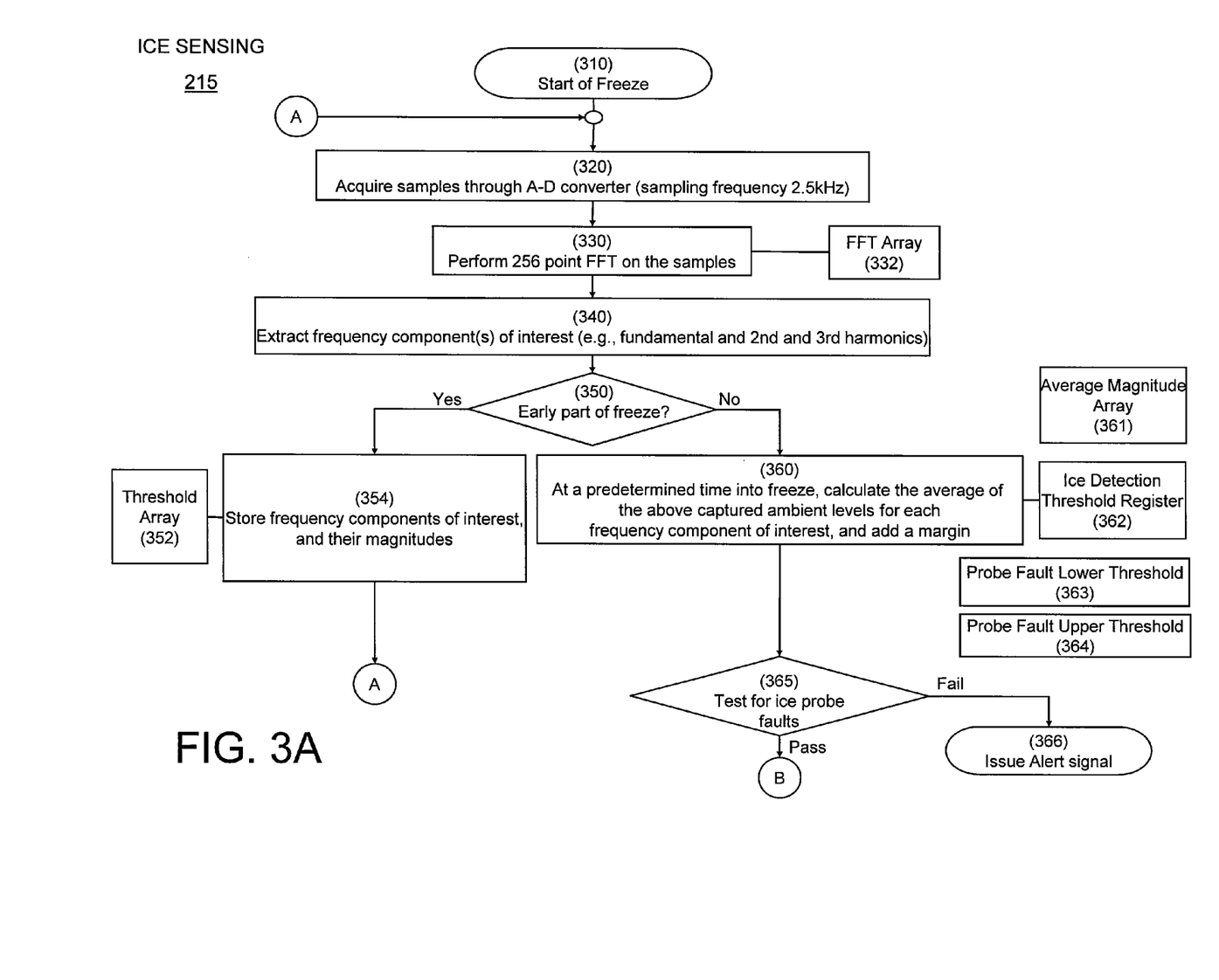
FIGS. 3A and 3B are, together, a flowchart of an ice-sensing process that is implemented on the control board of FIG. 2.
Figure 3B:
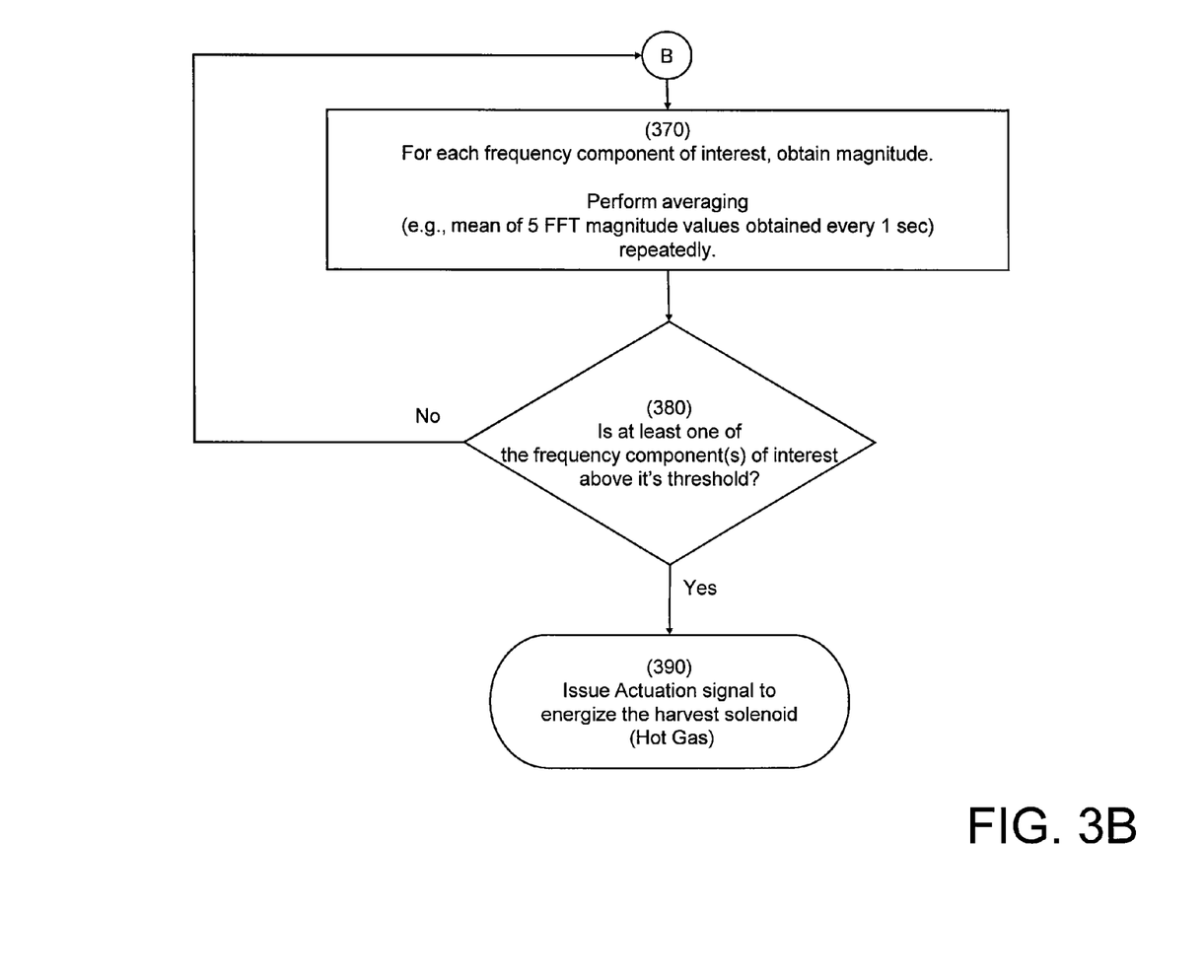

FIGS. 3A and 3B are, together, a flowchart of ice-sensing process 215. As mentioned above, in accordance with ice-sensing process 215, digital signal processing module 210 analyzes digital signal 208 to determine whether water 103 has formed into ice. Ice-sensing process 215 commences with step 310.

In step 310, system 100 starts its freeze stage. Accordingly, water 115 cascades over evaporator 102, and water 103 is being frozen. Sensor 110 detects acoustic wave 108, thus yielding detected acoustic wave 117, and microphone 140 converts detected acoustic wave 117 into analog electrical signal 122. From step 310, ice-sensing process 215 progresses to step 320.

In step 320, the A/D in micro-controller 205 samples analog electrical signal 122 at some sampling frequency, e.g., 2.5 kilohertz (kHz), and converts analog electrical signal 122 into digital signal 208. Detected acoustic wave 117 is a time-domain signal, i.e., magnitude as a function of time. Digital signal 208 is a digital representation of detected acoustic wave 117, and as such, is also a time-domain signal.

The magnitude of detected acoustic wave 117 is dependent upon the magnitude of acoustic wave 108, which is in turn dependent upon magnitudes of mechanical vibration 105 and mechanical vibration 107, and thus dependent on physical factors such as the size of system 100. As such, the magnitude of detected acoustic wave 117, and quantities derived from the magnitude of detected acoustic wave 117 are dependent on the size of system 100.

From step 320, ice-sensing process 215 progresses to step 330.

In step 330, digital signal processing module 210 transforms digital signal 208 from a time-domain signal to a frequency-domain signal, i.e., magnitude as a function of frequency. More specifically, digital signal processing module 210 performs an FFT on digital signal 208. The FFT determines frequency components, and their respective magnitudes, of detected acoustic wave 117. For example, digital signal processing module 210 performs a 256 point FFT and saves the frequency components and their respective magnitudes to an FFT array 332. From step 330, ice-sensing process 215 progresses to step 340.

In step 340, digital signal processing module 210 extracts one or more frequency components of interest, and their respective magnitudes, from FFT array 332. For example, digital signal processing module 210 extracts a fundamental frequency component, a second harmonic of the fundamental frequency component, and a third harmonic of the fundamental frequency component, and magnitudes for each of the fundamental frequency, second harmonic and third harmonic. The fundamental frequency would be, for example, either of a fundamental frequency of mechanical vibration 105 or a fundamental frequency of mechanical vibration 107. From step 340, ice-sensing process 215 progresses to step 350.

The fundamental frequency of mechanical vibration 105 and the fundamental frequency of mechanical vibration 107 may be inherent properties of compressor 104 and pump 106, and therefore, known in advance. Otherwise, these fundamental frequencies could be obtained through observation, or during a learning mode of ice-sensing process 215. For example, to learn the fundamental frequency of mechanical vibration 105, digital signal processing module 210, by way of communications with other components of system 100, would (a) turn OFF compressor 104 and evaluate a first spectrum of detected acoustic wave 117, and then (b) turn ON compressor 104 and evaluate a second spectrum of detected acoustic wave 117. The fundamental frequency of mechanical vibration 105 would appear as a dominant frequency component in the second spectrum, but not in the first spectrum. Alternatively, rather than digital signal processing module 210 controlling the ON/OFF states of compressor 104, system 100 may proceed in a regular mode of operation and notify digital signal processing module 210 when compressor 104 is ON or OFF.

In the next couple of steps, in the early part of the freeze stage, for example, within the first two minutes, before water 103 has formed as block of ice, digital signal processing module 210 obtains ambient acoustic levels of the frequencies of interest. Although in the present example, the early part of the freeze stage is regarded as a period of two minutes, other time durations are possible, e.g., six minutes.

In step 350, digital signal processing module 210 considers whether the freeze stage is in its early part. If the freeze stage is in its early part, then ice-sensing process 215 progresses from step 350 to step 354. If the freeze stage is not in its early part, then ice-sensing process 215 branches from step 350 to step 360.

In step 354, which is performed when the freeze stage is in its early part, digital signal processing module 210 stores the frequency components of interest, and their magnitudes, in a threshold array 352. From step 354, ice-sensing process 215 loops back to step 320.

By looping back to step 320, and progressing through steps 330, 340, 350 and 354, ambient acoustic levels of the frequencies of interest are repeatedly captured and stored in threshold array 352.

In step 360, which is performed when the freeze stage is not in its early part, for each of the frequencies of interest having magnitudes in threshold array 352, digital signal processing module 210 calculates an average magnitude, and stores the average magnitude in an average magnitude array 361. To the average magnitude, digital signal processing module 210 adds a margin, e.g. 3 decibels (dB), thus yielding a resultant threshold, and stores the resultant threshold into an ice detection threshold array 362. Ice detection threshold array 362 will thus hold a resultant threshold for each of the frequencies of interest. From step 360, ice-sensing process 215 progresses to step 365.

In step 365, digital signal processing module 210 tests for failures of sensor 110, microphone 140 (or the accelerometer being used in place of microphone 140) or, in the case of these components being integrated together, the sensing probe, collectively referred to as ice probe faults. Accordingly, for each of the frequency components of interest, digital signal processing module 210 calculates a standard deviation of the average magnitudes in average magnitude array 361. For each of the frequency components of interest, the standard deviation is compared to a probe fault lower threshold 363, and a probe fault upper threshold 364. If for any of the frequency components of interest, the standard deviation is less than probe fault lower threshold 363 or greater than probe fault upper threshold 364, there is assumed to be a fault of one or more of sensor 110, microphone 140 (or the accelerometer being used in place of microphone 140) or, in the case of these components being integrated together, the sensing probe. Although step 365 is being described as part of ice sensing process 215, it could be performed as part of system diagnostics 220.

As mentioned above, the magnitude of detected acoustic wave 117, and quantities derived from the magnitude of detected acoustic wave 117 are dependent on the size of system 100. Accordingly, appropriate values for probe fault lower threshold 363 and probe fault upper threshold 364 would be determined through experimentation.

From step 365, if the test passes, i.e., no fault is detected, then ice-sensing process 215 progresses to step 370. If the test fails, i.e., a fault is detected, then ice-sensing process 215 progresses to step 366.

In step 366, digital signal processing module 210 issues an ice probe fault alert, for example, by way of alert 165.

Although step 366 is being described as part of ice sensing process 215, it could be performed as part of system diagnostics 220.

In step 370, as water 103 continues to freeze, digital signal processing module 210 captures and processes real-time samples of detected acoustic wave 117. More specifically, digital signal processing module 210 extracts, from detected acoustic wave 117, frequency components of interest, and their respective magnitudes. For a better signal-to-noise ratio (SNR), and therefore better data integrity, average real-time magnitudes are considered over a period of time, e.g., mean of five FFT magnitude values obtained over a one-second interval of time. From step 370, ice-sensing process 215 progresses to step 380.

In step 380, digital signal processing module 210 compares the magnitudes of the real-time frequency components of interest to their corresponding magnitudes in ice detection threshold array 362. This comparison is being made because, when water 103 is adequately formed as a block of ice, the real-time magnitudes of the frequencies of interest will be significantly greater than they were before the ice was formed.

In step 380, if none of the real-time magnitudes is greater than its corresponding magnitude in ice detection threshold array 362, then digital signal processing module 210 concludes that water 103 is not yet sufficiently frozen, and digital signal processing module 210 loops back to step 370.

In step 380, if, for any of the frequency components of interests, the real-time magnitude is greater than its corresponding magnitude in ice detection threshold array 362, then digital signal processing module 210 concludes that water 103 is sufficiently frozen, and digital signal processing module 210 progresses to step 390.

Referring still to step 380, although the progression to step 390 is described as occurring in a case where, for any of the frequency components of interests, the real-time magnitude is greater than its corresponding magnitude in ice detection threshold array 362, the test can be based on some other minimum number of frequency components of interest having real-time magnitudes greater than their corresponding magnitudes in ice detection threshold array 362. For example, the test may require that at least two out of three frequency components of interest have real-time magnitudes greater than their corresponding magnitudes in ice detection threshold array 362.

In step 390, digital signal processing module 210 issues signal 124 to relay 150, which in turn issues actuation signal 155 to energize solenoid 160. Energizing solenoid 160 results in the harvesting, i.e., removing, of water 103, in the form of ice, from evaporator 102.

Figure 4:
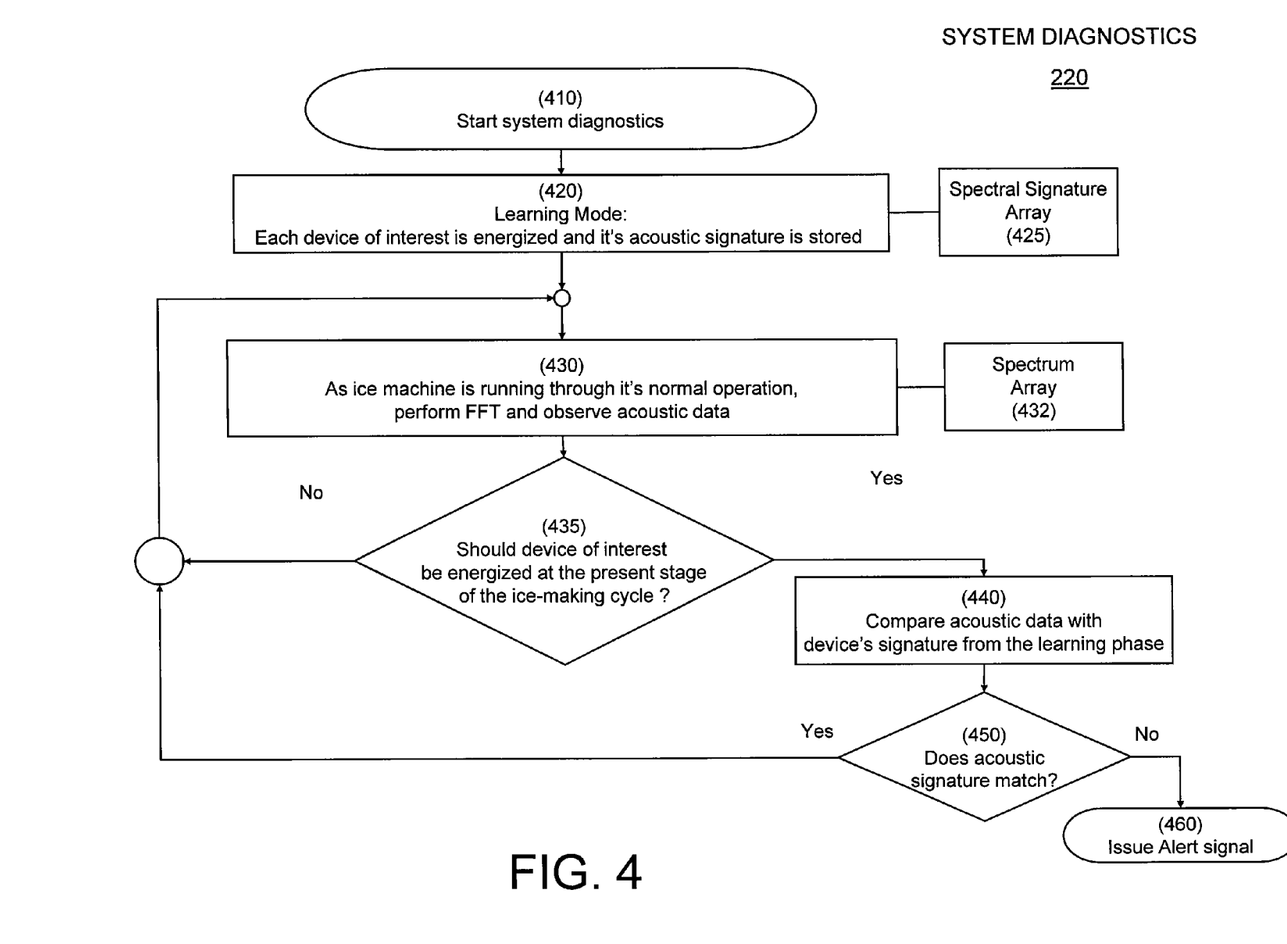
FIG. 4 is a flowchart of a system diagnostics process that is implemented on the control board of FIG. 2.

FIG. 4 is a flowchart of system diagnostics process 220. As mentioned above, in accordance with system diagnostics process 220, digital signal processing module 210 analyzes digital signal 208 to draw conclusions about the operations of compressor 104 and pump 106, and if necessary, issues alert signal 165. In brief, digital signal processing module 210 evaluates acoustic signatures of devices within system 100 to determine whether or not the devices are energizing at appropriate times. Below, system diagnostics process 220 is described with regard to operations of compressor 104 and pump 106. However, system diagnostics process 220 can be employed to evaluate operations of any device in system 100 that generates a mechanical vibration (e.g., a dump valve, a harvest solenoid, and a water inlet valve). System diagnostics process 220 commences with step 410.

In step 410, system diagnostics process 220 commences operation. From step 410, system diagnostics process 220 progresses to step 420.

In step 420, digital signal processing module 210 operates in a learning mode in which digital signal processing module 210 analyzes and records mechanical vibrations produced by compressor 104 and pump 106. For example, by way of communications with other components of system 100, digital signal processing module 210 energizes, or is notified of the energization of, compressor 104. Compressor 104 generates mechanical vibration 105, which is manifested in acoustic wave 108, and detected by sensor 110, to produce detected acoustic wave 117. Digital signal processing module 210 analyzes detected acoustic wave 117 to obtain a spectral signature, i.e., frequency components and magnitudes, of compressor 104. Digital signal processing module 210, in a similar manner, obtains a spectral signature of pump 106. Digital signal processing module 210 stores the spectral signatures for each of compressor 104 and pump 106 in a spectral signature array 425. From step 420, system diagnostics process 220 progresses to step 430.

In step 430, as system 100 is running through its normal ice-making cycle (i.e., pre-chill, freeze, harvest and purge), digital signal processing module 210 performs FFTs and observes acoustic data. More specifically, digital signal processing module 210 analyzes detected acoustic wave 117 to yield a spectrum thereof. Digital signal processing module 210 stores the spectrum in a spectrum array 432. From step 430, system diagnostics process 220 progresses to step 435.

In step 435, digital signal processing module 210 considers whether either of compressor 104 or pump 106 should be energized in the present stage of the ice-making cycle. That is, digital signal processing module 210, by way of communications with other components of system 100, knows whether either of compressor 104 or pump 106 should be energized. If either of compressor 104 or pump 106 should not be energized, then system diagnostics process 220 loops back to step 430. If either of compressor 104 or pump 106 should be energized, then system diagnostics process 220 progresses to step 440.

In step 440, digital signal processing module 210 determines whether the spectrum from step 430 includes a spectral signature of the device, i.e., compressor 104 or pump 106, that should be energized. For example, assume that compressor 104 should be energized. Accordingly, digital signal processing module 210 determines whether spectrum array 432 includes the spectral signature of compressor 104 that is stored in spectral signature array 425. From step 440, system diagnostics process 220 progresses to step 450.

In step 450, if spectrum array 432 includes the spectral signature of the device being considered, e.g., compressor 104, then digital signal processing module 210 concludes that system 100 is operating properly, and accordingly system diagnostics process 220 loops back to step 430. If spectrum array 432 does not include the spectral signature of the device being considered, then digital signal processing module 210 concludes that system 100 is not operating properly, and accordingly system diagnostics process 220 progresses to step 460.

Referring still to step 450, recall that spectral signature array 425 contains a spectral signature for each of compressor 104 and pump 106. Accordingly, digital signal processing module 210 can therefore determine whether detected acoustic signal 117 includes either or both of mechanical vibration 105 and mechanical vibration 107. This also enables system diagnostics process 220 to distinguish between spectral contributions from compressor 104 and pump 106, and determine whether either or both of compressor 104 and pump 106 is ON, and therefore diagnose operations of either or both of compressor 104 and pump 106. Moreover, digital signal processing module 210 can make these determinations even in a case where detected acoustic signal 117 includes noise or spectral contributions from other devices in system 100.

In step 460, digital signal processing module 210 issues alert signal 165.

Digital signal processing module 210 is described above as issuing alert signal 165 for a case where a device that is being considered is expected to be ON, but spectrum array 432 does not include the spectral signature of the device being considered. However, system diagnostics process 220 could be configured so that digital signal processing module 210 issues alert signal 165 in a case where a device is expected to be OFF, and so, the spectrum should not include the spectral signature of the device, but instead spectrum array 432 does include the spectral signature of the device. This situation could occur, for example, in a case where either system 100 fails to turn OFF the device, or the device is stuck in its ON state.

In review, system 100 includes a detector, i.e., sensor 110, and a processor, i.e., processing module 145. Sensor 110 detects acoustic wave 108, which is propagating through a body of water, i.e., water 103, as water 103 is being frozen on a structure, i.e., evaporator 102, in an ice-making machine, thus yielding detected acoustic wave 117.

Processing module 145: extracts, from detected acoustic wave 117, (a) a frequency component thereof, and (b) a magnitude of the frequency component; and issues a signal, i.e., signal 124, to remove water 103 from evaporator 102 when the magnitude exceeds a threshold value.

Processing module 145 also: analyzes detected acoustic wave 117 to yield a spectrum thereof; determines whether the spectrum includes a spectral signature, thus yielding a determination, wherein the spectral signature is present when a device, e.g., compressor 104, in the ice-making machine is operating; and issues an alert, i.e., alert signal 165, based on the determination.

Detected acoustic wave 117 is a time-domain signal. Processing module 145, to extract the frequency component and the magnitude: transforms the time-domain signal to a frequency-domain signal; and obtains the frequency component, and the magnitude, from the frequency-domain signal.

Also in system 100, the threshold value against which the magnitude is compared may be regarded as a first threshold value, and accordingly, processing module 145: also extracts, from detected acoustic wave 117, (a) a harmonic of the frequency component, and (b) a magnitude of the harmonic; and issues signal 124 to relay 150 when both of (i) the magnitude exceeds the first threshold value, and (ii) the magnitude of the harmonic exceeds a second threshold value.

System 100 is described above with processing module 145 being implemented on control board 130. As such, processing module 145, or any of its components, and in particular digital signal processing module 210, may be implemented in hardware (e.g., electronic circuitry) or firmware, or a combination thereof. Moreover, digital signal processing module 210 can be implemented in software, and run on a computer that is in communication with other components in system 100.

Figure 5:
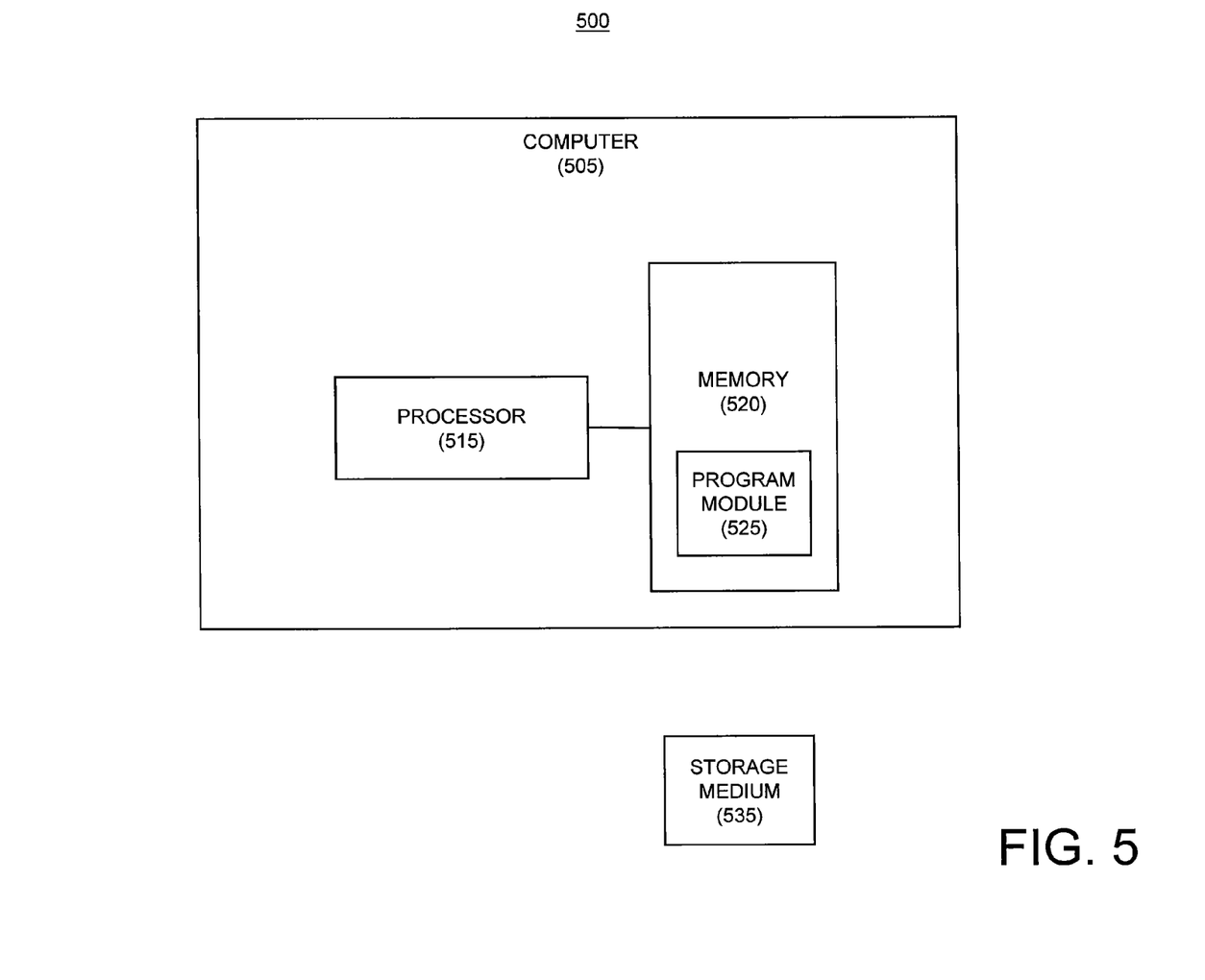
FIG. 5 is a block diagram of a system that executes the operations of the ice-sensing process of FIG. 2 and the system diagnostics process of FIG. 3.

FIG. 5 is a block diagram of a computer-implemented embodiment, hereinafter referred to as system 500, of digital signal processing module 210. System 500 includes a computer 505 that in turn includes a processor 515 and a memory 520. System 500 is in communication with other components in system 100.

Processor 515 is an electronic device configured of logic circuitry that responds to and executes instructions.

Memory 520 is a computer-readable medium encoded with a computer program. In this regard, memory 520 stores data and instructions that are readable and executable by processor 515 for controlling the operation of processor 515. Memory 520 may be implemented in a random access memory (RAM), a hard drive, a read only memory (ROM), flash memory, or a combination thereof. One of the components of memory 520 is a program module 525.

Program module 525 contains instructions for controlling processor 515 to execute the methods described herein. That is, instructions from program module 525, when read by processor 515, cause processor 515 to perform operations of ice-sensing process 215, and system diagnostics process 220.

Although program module 525 is described herein as being installed in memory 520, and therefore being implemented in software, it could be implemented in any of hardware (e.g., electronic circuitry), firmware, software, or a combination thereof.

Processor 515 outputs a result of an execution of the methods described herein, for example, a fault indicator based on the issuance of alert signal 165. Alternatively, processor 515 could direct the output to a remote device (not shown) via a network (not shown).

While program module 525 is indicated as being already loaded into memory 520, it may be configured on a storage medium 535 for subsequent loading into memory 520. Storage medium 535 is also a computer-readable medium that stores program module 525 thereon. Examples of storage medium 535 include a floppy disk, a compact disk, a magnetic tape, a read only memory, an optical storage media, universal serial bus (USB) flash drive, a digital versatile disc, or a zip drive. Alternatively, storage medium 535 can be a random access memory, or other type of electronic storage, located on a remote storage system and coupled to computer 505 via a network (not shown).

As mentioned above, microphone 140 and sensor 110 could be integrated together, thus resulting in an integrated sensor microphone, and an alternative to the integrated sensor microphone is an integrated sensor accelerometer that employs an accelerometer instead of microphone 140. Either of integrated sensor microphone or the integrated sensor accelerometer could be regarded as a sensing probe.

Figure 6:
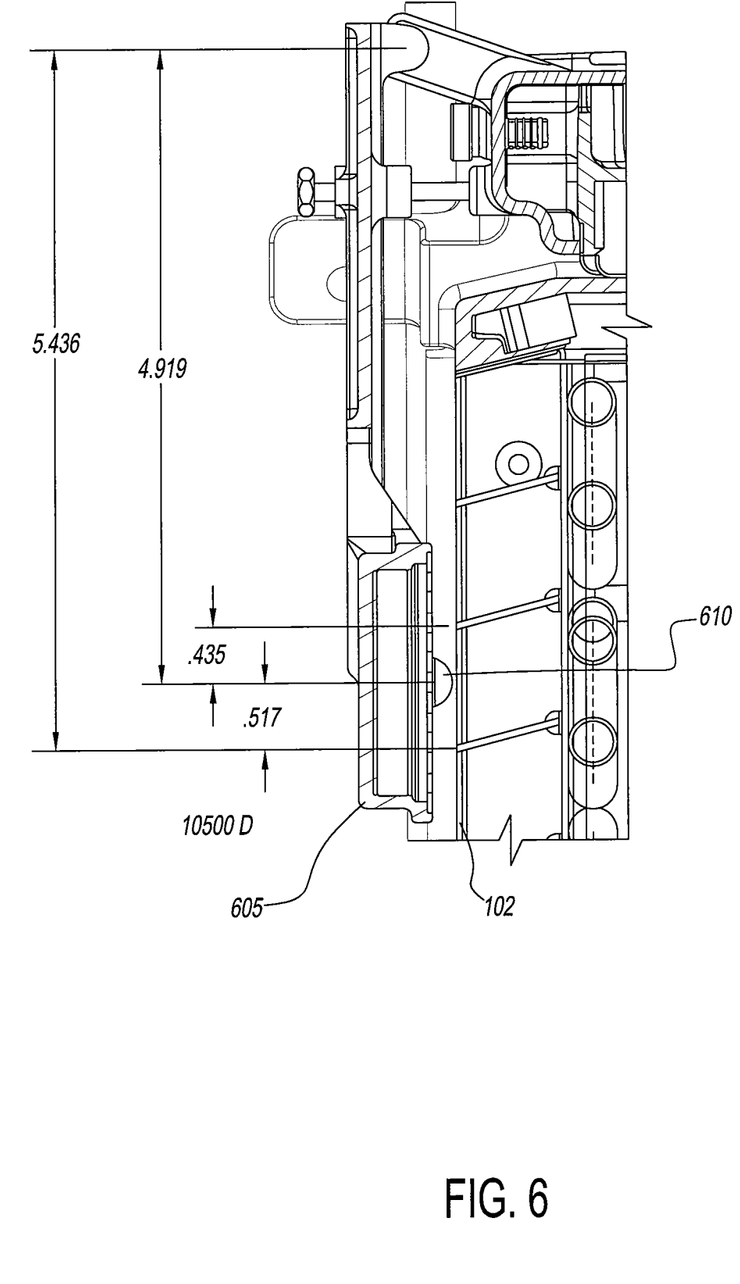
FIG. 6 is a cross-section view of a probe on an evaporator.

FIG. 6 is a cross-section view of a sensing probe 605 on evaporator 102. Sensing probe 605 includes a dimple 610 that is implemented as a part of sensor 110 and that contacts water 103 on evaporator 102.

Figure 7:
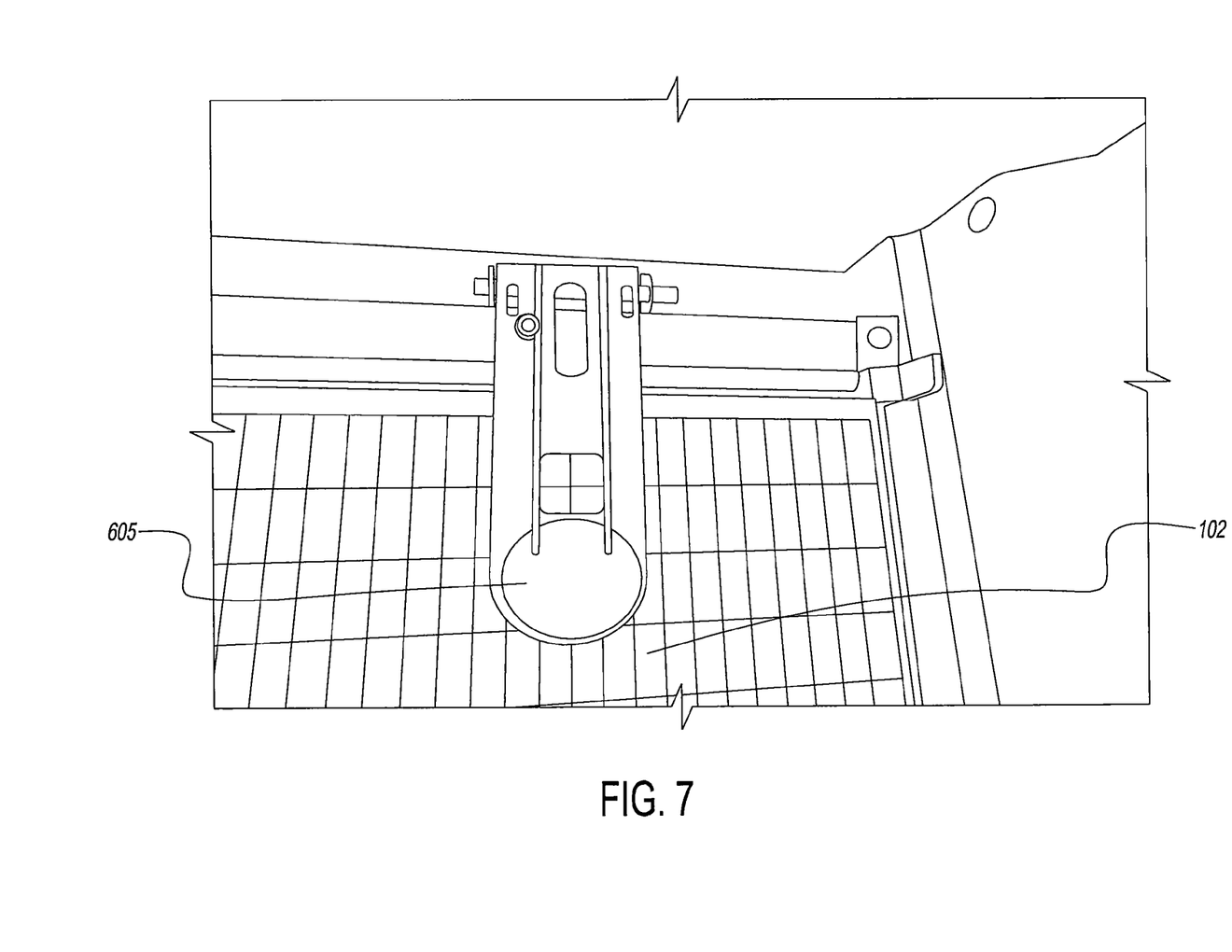
FIG. 7 is a picture of a probe mounted to an evaporator.

FIG. 7 is a picture of sensing probe 605 on evaporator 102.

Figure 8:
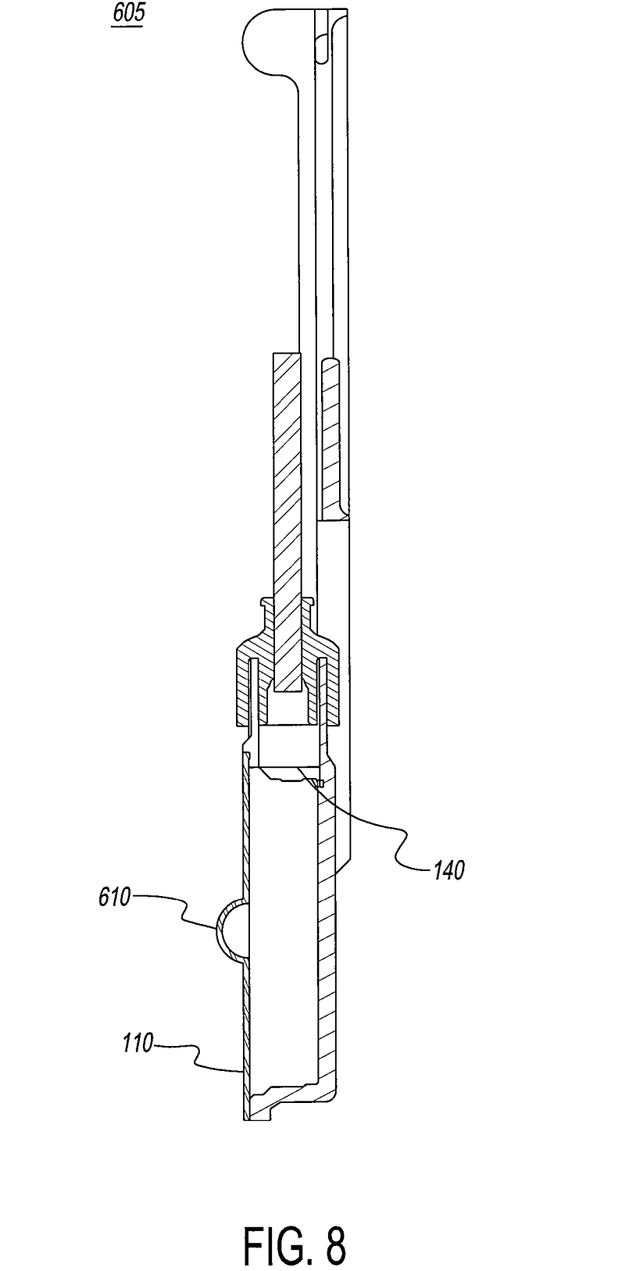
FIG. 8 is a side view of an integrated sensor microphone.

FIG. 8 is a cross-section view of sensing probe 605 configured as an integrated sensor microphone having microphone 140 embedded into a top opening.

The techniques described herein are exemplary, and should not be construed as implying any particular limitation on the present disclosure. It should be understood that various alternatives, combinations and modifications could be devised by those skilled in the art. For example, system 100 may include a plurality of sensors 110 for detecting acoustic wave 108 at various locations on water 103, and steps associated with the processes described herein can be performed in any order, e.g., order of steps 435 and 430 can be reversed, unless otherwise specified or dictated by the steps themselves. Also, although acoustic wave 108 is described herein as resulting from mechanical vibrations of either compressor 105 or pump 107, system 100 could include a special-purpose device that generates a particular vibration for analysis by processing module 145. The present disclosure is intended to embrace all such alternatives, modifications and variances that fall within the scope of the appended claims.

The terms "comprises" or "comprising" are to be interpreted as specifying the presence of the stated features, integers, steps or components, but not precluding the presence of one or more other features, integers, steps or components or groups thereof.

What is claimed is:

1. A method comprising:
   detecting an acoustic wave that is propagating through a body of water, as said body of water is being frozen on a structure, thus yielding a detected acoustic wave;
   extracting, from said detected acoustic wave, (a) a frequency component thereof, (b) a magnitude of said frequency component, (c) a harmonic of said frequency component, and (d) a magnitude of said harmonic; and
   removing said body of water from said structure when both of (i) said magnitude of said frequency component exceeds a first threshold value, and (ii) said magnitude of said harmonic exceeds a second threshold value.

2. The method of claim 1,
   wherein said detected acoustic wave is a time-domain signal, and
   wherein said extracting comprises:
      transforming said time-domain signal to a frequency-domain signal; and
      obtaining said frequency component, said magnitude of said frequency component, said harmonic, and said magnitude of said harmonic, from said frequency-domain signal.

3. A system comprising:
   a detector that detects an acoustic wave that is propagating through a body of water, as said body of water is being frozen on a structure, thus yielding a detected acoustic wave; and
   a processor that:
      extracts, from said detected acoustic wave, (a) a frequency component thereof, (b) a magnitude of said frequency component, (c) a harmonic of said frequency component, and (d) a magnitude of said harmonic; and
      issues a signal to remove said body of water from said structure when both of (i) said magnitude of said frequency component exceeds a first threshold value, and (ii) said magnitude of said harmonic exceeds a second threshold value.

4. The system of claim 3,
   wherein said detected acoustic wave is a time-domain signal, and
   wherein said processor, to extract said frequency component and said magnitude:
      transforms said time-domain signal to a frequency-domain signal; and
      obtains said frequency component, said magnitude of said frequency component, said harmonic, and said magnitude of said harmonic, from said frequency-domain signal.

5. The system of claim 3, wherein said detector comprises a microphone in a probe that is situated less than 0.5 inches from said structure.

6. The system of claim 3, wherein said detector comprises a microphone in a probe that is in contact with said structure.

7. The system of claim 3, wherein said detector comprises a microphone in a probe that is situated less than 0.5 inches from said body of water.

8. The system of claim 3, wherein said detector comprises a microphone in a probe that is in contact with said body of water.

9. A non-transitory computer-readable storage medium comprising instructions that are readable by a processor, and that when read by said processor cause said processor to:
   extract, from a detected acoustic wave, (a) a frequency component thereof, (b) a magnitude of said frequency component, wherein said detected acoustic wave represents an acoustic wave that is propagating through a body of water, as said body of water is being frozen on a structure, (c) a harmonic of said frequency component, and (d) a magnitude of said harmonic; and
   issue a signal to remove said body of water from said structure when both of (i) said magnitude exceeds a threshold value, and (ii) said magnitude of said harmonic exceeds a second threshold value.

10. The non-transitory computer-readable storage medium of claim 9, wherein said detected acoustic wave is a time-domain signal, and
    wherein said processor, to extract said frequency component and said magnitude:
       transforms said time-domain signal to a frequency-domain signal; and
       obtains said frequency component, said magnitude of said frequency component, said harmonic, and said magnitude of said harmonic, from said frequency-domain signal.

* * * * *